United States Patent
Tanaka

(10) Patent No.: US 11,321,814 B2
(45) Date of Patent: May 3, 2022

(54) IMAGE PROCESSING DEVICE, IMAGE PROCESSING METHOD, AND COMPUTER READABLE RECORDING MEDIUM

(71) Applicant: Sony Olympus Medical Solutions Inc., Tokyo (JP)

(72) Inventor: Akihisa Tanaka, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 29 days.

(21) Appl. No.: 16/729,523

(22) Filed: Dec. 30, 2019

(65) Prior Publication Data

US 2020/0294200 A1    Sep. 17, 2020

(30) Foreign Application Priority Data

Mar. 15, 2019    (JP) .............................. JP2019-049084

(51) Int. Cl.
*G06T 5/00* (2006.01)
*G06T 5/50* (2006.01)

(52) U.S. Cl.
CPC ................ *G06T 5/002* (2013.01); *G06T 5/50* (2013.01); *G06T 2207/10064* (2013.01); *G06T 2207/10068* (2013.01); *G06T 2207/20182* (2013.01)

(58) Field of Classification Search
CPC .......... G06T 5/002; G06T 5/50; G06T 5/008; G06T 5/005; G06T 5/00; G06T 5/001; G06T 5/30; G06T 7/0012; G06T 7/136; G06T 2207/10068; G06T 2207/20182; G06T 2207/10064; G06T 2207/30004; G06T 2207/10121; G06T 2207/20172; G06T 2207/20216; G06T 2207/20221; G06T 2207/20224; G06T 2207/30028; G06T 2207/30032; G06T 2207/30092; G06T 2210/41; A61B 1/00006; A61B 1/005; A61B 1/0684; A61B 1/0638; A61B 1/045; A61B 1/042; A61B 1/00009; A61B 1/043; A61B 1/063; A61B 1/0669; A61B 1/0005; A61B 1/00; A61B 2576/00; G01N 21/64; G01N 21/6456; G02B 23/2461;
(Continued)

(56) References Cited

U.S. PATENT DOCUMENTS

2014/0153842 A1* 6/2014 Pescatore ................ G06T 5/002
                                                        382/264
2014/0184769 A1* 7/2014 Ishihara .................... G06T 5/50
                                                        348/68

(Continued)

*Primary Examiner* — Jose L Couso
(74) *Attorney, Agent, or Firm* — Xsensus LLP

(57) ABSTRACT

An image processing device includes: a memory; and a processor comprising hardware, wherein the processor is configured to: receive agent observation image information including information of a plurality of pixels obtained by capturing an image based on fluorescence from a subject administered with an agent that emits fluorescence upon being irradiated with excitation light in a predetermined wavelength band; amplify pixel values of the plurality of pixels by executing first gain processing on the agent observation image information; and reduce pixel values of pixels lower than a predetermined threshold by executing reduction processing on the agent observation image information after the first gain processing.

11 Claims, 10 Drawing Sheets

(58) Field of Classification Search
CPC ............. G02B 23/2484; H04N 5/2256; H04N 2005/2255
See application file for complete search history.

(56) References Cited

U.S. PATENT DOCUMENTS

| | | | |
|---|---|---|---|
| 2014/0221745 A1* | 8/2014 | Yamaguchi | G06T 7/136 600/109 |
| 2015/0016705 A1* | 1/2015 | Kubo | A61B 1/043 382/132 |
| 2016/0269611 A1* | 9/2016 | Kutsuma | H04N 5/243 |
| 2019/0099081 A1* | 4/2019 | Horesh | A61B 1/043 |

* cited by examiner

IMAGE PROCESSING DEVICE, IMAGE PROCESSING METHOD, AND COMPUTER READABLE RECORDING MEDIUM

This application claims priority from Japanese Application No. 2019-049084, filed on Mar. 15, 2019, the contents of which are incorporated by reference herein in its entirety.

BACKGROUND

The present disclosure relates to an image processing device, an image processing method, and a computer readable recording medium.

In the related art, a technique for preventing deterioration in image quality for endoscopes has been known. Specifically, noise removal processing is executed on a white image and a fluorescent image with different noise removal levels respectively set for the white image and the fluorescent image, before the images are output to a processor that executes image processing (see, for example, JP 2009-95525 A). According to this technique, the noise removal is performed, with the noise removal level set to be higher for the fluorescent image than that for the white image, in the following manner.

Specifically, a plurality of fluorescent images in time sequence is each multiplied by a weight coefficient, and the resultant values are averaged. Furthermore, there has been known a technique of performing noise removal by calculating, for each pixel in the white image and the fluorescent image, an average value of a pixel value of the pixel and pixel values of neighboring pixels.

SUMMARY

However, in JP 2009-95525 A described above, there is a problem that a plurality of fluorescent images in time sequence need to be prepared for the noise averaging to be performed, which leads to a moving image with poor responsiveness involving notable afterimage.

Furthermore, the above-mentioned method of calculating an average value of a pixel value of each pixel and pixel values of neighboring pixels has a problem that results in compromised resolution.

There is a need for an image processing device, an image processing method, and a computer readable recording medium capable of suppressing resolution degradation and preventing notable afterimage from being produced.

According to one aspect of the present disclosure, there is provided an image processing device including: a memory; and a processor comprising hardware, wherein the processor is configured to: receive agent observation image information including information of a plurality of pixels obtained by capturing an image based on fluorescence from a subject administered with an agent that emits fluorescence upon being irradiated with excitation light in a predetermined wavelength band; amplify pixel values of the plurality of pixels by executing first gain processing on the agent observation image information; and reduce pixel values of pixels lower than a predetermined threshold by executing reduction processing on the agent observation image information after the first gain processing.

DETAILED DESCRIPTION

Figure 1:
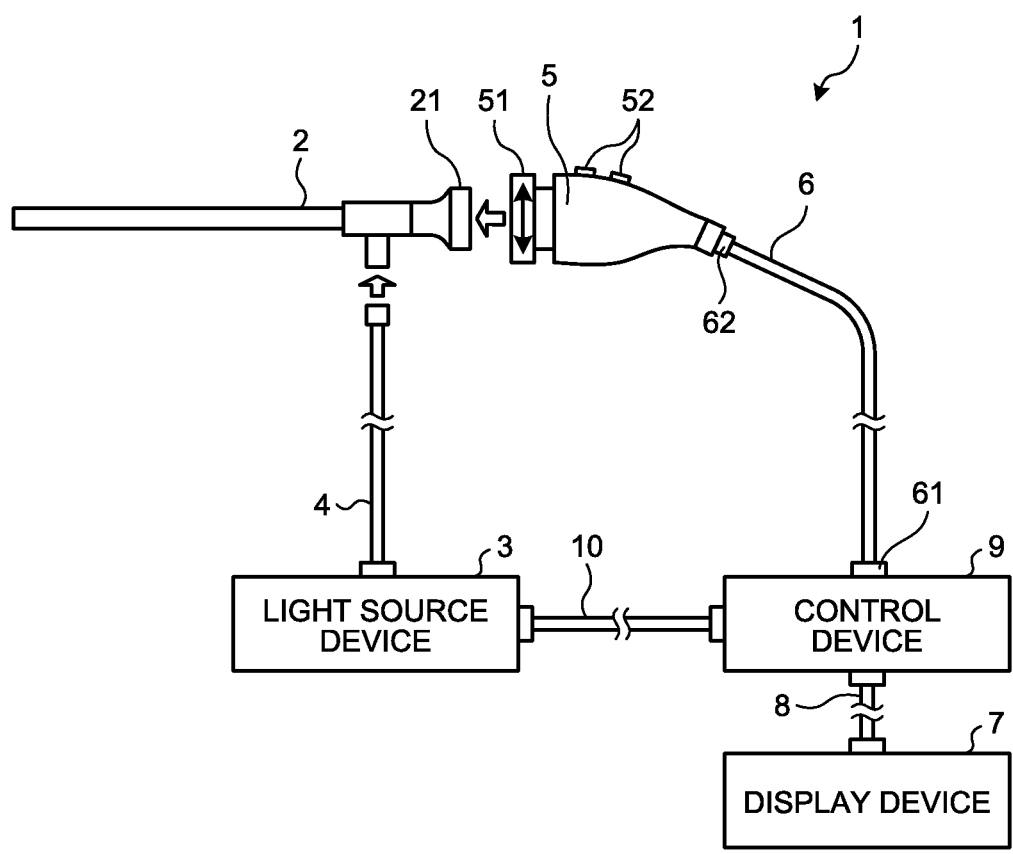
FIG. 1 is a diagram illustrating a schematic configuration of an endoscope system according to a first embodiment.

Hereinafter, modes for carrying out the present disclosure (hereinafter referred to as "embodiments") will be described in detail with reference to the drawings. Note that the present disclosure is not limited to the following embodiments. Furthermore, drawings referred to in the following description are illustrated with schematic shape, size, and positional relationship only sufficient for understanding the content of the present disclosure. Thus, the present disclosure is not limited only to the shape, size, and positional relationship illustrated in each drawing. Furthermore, in the drawings, the same components are denoted with the same reference numerals. Furthermore, an endoscope system will be described as an example of a medical observation system according to the present disclosure.

First Embodiment

FIG. 1 is a diagram illustrating a schematic configuration of an endoscope system according to a first embodiment. An endoscope system 1 illustrated in FIG. 1, used in the medical field, is inserted into a subject (into a living body) such as a living human or animal body, and captures and displays in-vivo images, so that the subject may be observed. Note that in the first embodiment, a rigid endoscope system using a rigid endoscope (insertion portion 2) illustrated in FIG. 1 will be described as the endoscope system 1. However, the present disclosure is not limited to this, and the endoscope system 1 may be a flexible endoscope system, for example.

The endoscope system 1 illustrated in FIG. 1 includes the insertion portion 2 (endoscope), a light source device 3, a light guide 4, a camera head 5 (endoscopic image capturing device), a first transmission cable 6, a display device 7, a second transmission cable 8, a control device 9, and a third transmission cable 10.

The insertion portion 2, inserted into a subject such as a patient, is rigid or at least partially flexible and has an elongated shape. The insertion portion 2 incorporates an optical system that includes one or a plurality of lenses and forms an observation image.

The light source device 3 is connected with one end of the light guide 4. Under the control of the control device 9, the light source device 3 emits (supplies), to the one end of the light guide 4, white light for illuminating the inside of the subject and excitation light or infrared light to the agent administered to or dispersed in the subject. The light source device 3 is configured to include a semiconductor laser element such as a light emitting diode (LED) light source or a laser diode (LD). The light source device 3 and the control device 9 may be configured to be individual devices that communicate with each other as illustrated in FIG. 1, or may be configured to be integrated.

The light guide 4 has the one end detachably connected to the light source device 3, and the other end detachably connected to the insertion portion 2. The light guide 4 guides the light emitted from the light source device 3 from the one end to the other end and supplies the light to the insertion portion 2.

The camera head 5 is detachably connected to an eyepiece 21 of the insertion portion 2. Under the control of the control device 9, the camera head 5 captures an observation image formed by the insertion portion 2 to generate a captured image signal and outputs this captured image signal (electric signal). In addition, the camera head 5 includes an operation ring unit 51 that is provided to be rotatable in a circumferential direction, and a plurality of input units 52 that receive input of instruction signals for instructing various operations of the endoscope system 1.

The first transmission cable 6 has one end detachably connected to the control device 9 via a first connector unit 61 and the other end connected to the camera head 5 via a second connector unit 62. The first transmission cable 6 transmits the captured image signal output from the camera head 5 to the control device 9, and transmits a control signal, a synchronization signal, a clock signal, power, and the like output from the control device 9 to the camera head 5.

The display device 7 may be connected to the control device 9 via the second transmission cable 8. Under the control of the control device 9, the display device 7 displays a display image based on agent observation image information or subject observation image information processed by the control device 9.

The second transmission cable 8 has one end detachably connected to the display device 7 and the other end detachably connected to the control device 9. The second transmission cable 8 transmits the display image based on the agent observation image information or the subject observation image information processed by the control device 9, to the display device 7.

The control device 9 is configured to include a memory and a processor with hardware including a central processing unit (CPU), a graphics processing unit (GPU), an application specific integrated circuit (ASIC), and a field programmable gate array (FPGA), and performs overall control on operations performed by the camera head 5, the display device 7, and the light source device 3, respectively via the first transmission cable 6, the second transmission cable 8, and the third transmission cable 10, in accordance with a program stored in the memory.

The third transmission cable 10 has one end detachably connected to the light source device 3 and the other end side detachably connected to the control device 9. The third transmission cable 10 transmits the control signal from the control device 9 to the light source device 3.

Detailed configuration of light source device, camera head, and control device

Figure 2:
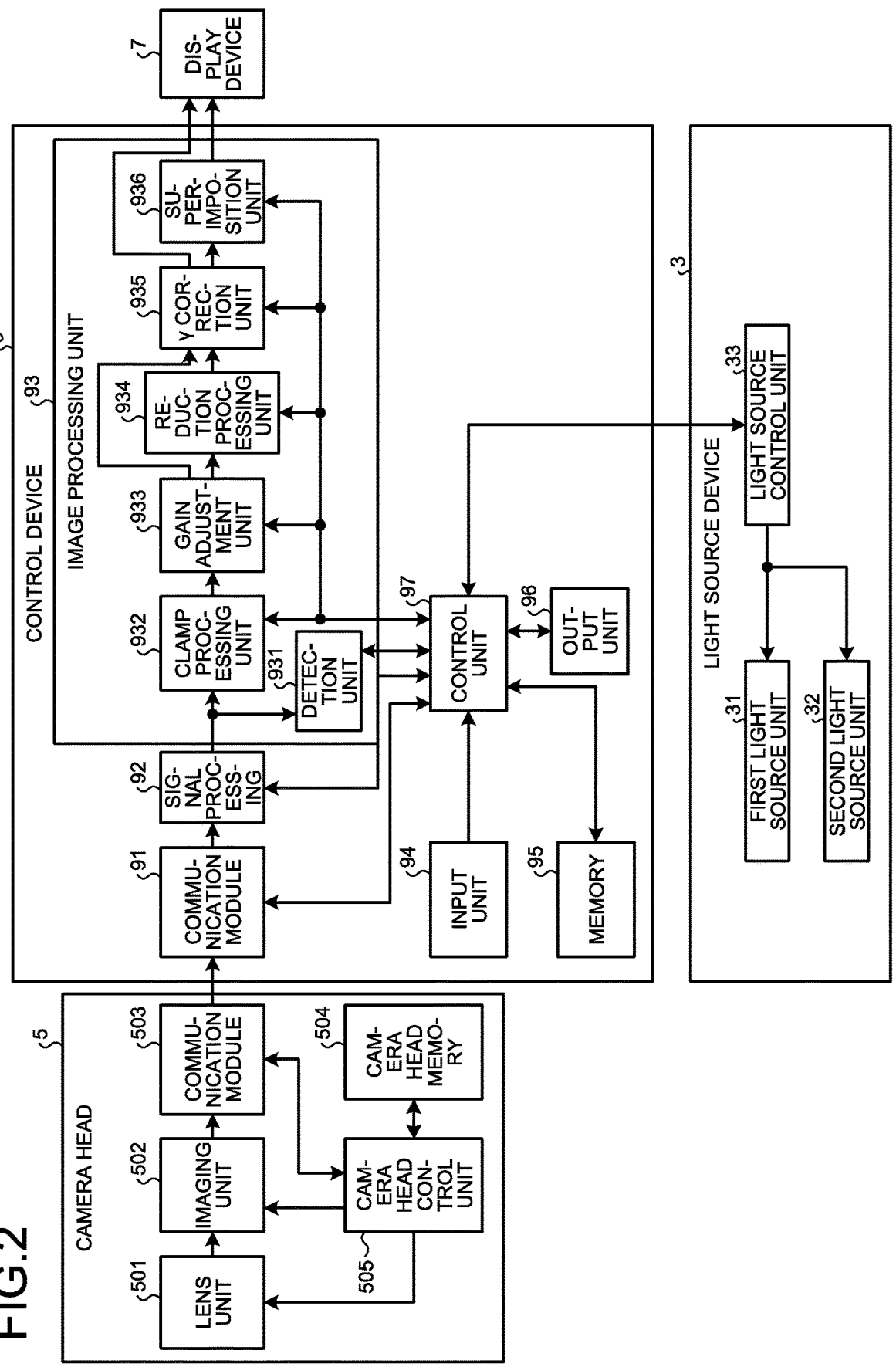
FIG. 2 is a block diagram illustrating functional configurations of a light source device, a camera head, and a control device included in the endoscope system according to the first embodiment.

Next, functional configurations of the light source device 3, the camera head 5, and the control device 9 will be described. FIG. 2 is a block diagram illustrating functional configurations of the light source device 3, the camera head 5, and the control device 9 included in the endoscope system 1. Note that in FIG. 2, the insertion portion 2, the light guide 4, the first transmission cable 6, the second transmission cable 8, and the third transmission cable 10 are omitted for the sake of illustration.

Configuration of Light Source Device

First of all, the configuration of the light source device 3 will be described.

The light source device 3 includes a first light source unit 31, a second light source unit 32, and a light source control unit 33.

The first light source unit 31 is capable of pulsed light emission, and emits and supplies, to the insertion portion 2, white light with which the subject is irradiated via the insertion portion 2. Specifically, the first light source unit 31 emits and supplies, to the insertion portion 2, white light in a subject observation mode for capturing an image based on reflected light from the subject, under the control of the light source control unit 33. The first light source unit 31 is configured to include a red semiconductor laser element that may emit red (wavelength band 600 nm to 700 nm) light, a blue semiconductor laser element that may emit blue (wavelength band 400 nm to 500 nm) light, and a green semiconductor laser element that may emit green (wavelength band 500 nm to 600 nm) light. Note that the first light source unit 31 is configured to include the red, the blue, and the green semiconductor laser elements. However, the first light source unit 31 is not limited to this, and may include a white semiconductor laser element that may emit white light. Furthermore, the first light source unit 31 does not have to be a semiconductor laser element as long as pulse light emission may be implemented, and may be, for example, a light emitting diode (LED) or the like.

The second light source unit 32 is capable of pulse light emission, and emits infrared light with which the subject is irradiated via the insertion portion 2. Specifically, under the control of the light source control unit 33, the second light source unit 32 excites the agent (fluorescent substance) administered into the subject and emits and supplies, to the insertion portion 2, infrared light (wavelength band 700 to 1000 nm) in an agent observation mode for capturing an image based on light emitted from the agent. The second light source unit 32 is configured to include a semiconductor laser element that may emit light (700 to 1000 nm) for exciting the fluorescent substance, a filter through which light in a certain wavelength band may pass, and the like. Note that in the following description, the second light source unit 32 emits infrared light. However, this should not be construed in a limiting sense, and the second light source unit 32 may emit light (wavelength band around 405 nm) used for photo dynamic diagnosis (PDD) observation for observing fluorescence with a photosensitive substance (such as hematoporphyrin derivative) accumulated in a tumorous tissue in advance, light (wavelength band 390 to 470 nm+wavelength band 540 to 560 nm) used for auto fluorescence imaging (AFI) observation in which light emitted from a fluorescent substance such as collagen is observed, and the other like light, for example.

The light source control unit 33 controls light emission of the first light source unit 31 and the second light source unit 32 under the control of the control device 9. The light source control unit 33 is configured to include a memory and a processor having hardware such as a CPU, an ASIC, and an FPGA.

Configuration of Camera Head

Next, a configuration of the camera head 5 will be described.

The camera head 5 includes a lens unit 501, an imaging unit 502, a communication module 503, a camera head memory 504, and a camera head control unit 505.

The lens unit 501 is configured to include one or a plurality of lenses, and forms an object image on a light receiving surface of the imaging unit 502. In addition, under control of the camera head control unit 505, the lens unit 501 performs auto focus (AF) of changing a focal position and optical zooming of changing a focal length, with an unillustrated driver moving the lens(es) along an optical axis direction. Note that in the first embodiment, the lens unit 501 may be provided with a diaphragm mechanism and an optical filter mechanism that may be inserted on and removed from the optical axis.

The imaging unit 502 (image sensor) receives the object image formed by the insertion portion 2 and the lens unit 501 under the control of the camera head control unit 505, and performs photoelectric conversion to obtain a captured image signal (RAW data). The imaging unit 502 outputs this captured image signal to the communication module 503. The imaging unit 502 outputs a captured image signal generated in the agent observation mode in which the second light source unit 32 irradiates the agent administered to the subject with infrared light, to the communication module 503 as the agent observation image information. Furthermore, the imaging unit 502 outputs a captured image signal generated in the subject observation mode in which the first light source unit 31 irradiates the subject with light and captures an image based on the light reflected from the subject, to the communication module 503 as the subject observation image information. The imaging unit 502 is configured to include a charge coupled device (CCD), a complementary metal oxide semiconductor (CMOS), or the like.

The communication module 503 outputs various signals transmitted from the control device 9 via the first transmission cable 6 to the units of the camera head 5. Furthermore, the communication module 503 performs parallel-serial conversion processing or the like on the agent observation image information and the subject observation image information generated by the imaging unit 502, information on the current state of the camera head 5, and the like, and outputs the resultant information to the control device 9 via the first transmission cable 6.

The camera head memory 504 stores camera head information for identifying the camera head 5 and various programs executed by the camera head 5. This camera head information includes the number of pixels of the imaging unit 502, the pixel pitch, the identification ID of the camera head 5, and the like. The camera head memory 504 is configured to include a volatile memory, a nonvolatile memory, and the like.

The camera head control unit 505 controls the operation of the units configuring the camera head 5, based on various signals input from the communication module 503. The camera head control unit 505 is configured to include a memory and a processor having hardware such as a CPU.

Configuration of Control Device

Next, a configuration of the control device 9 will be described.

The control device 9 includes a communication module 91, a signal processing unit 92, an image processing unit 93, an input unit 94, a memory 95, an output unit 96, and a control unit 97.

The communication module 91 outputs various signals, including the captured image signal input from the camera head 5, to the control unit 97 and the signal processing unit 92. Furthermore, the communication module 91 transmits various signals input from the control unit 97 to the camera head 5. Specifically, the communication module 91 executes parallel-serial conversion processing or the like on the signal input from the control unit 97 and outputs the resultant signal to the camera head 5. Furthermore, the communication module 91 executes serial-parallel conversion processing or the like on the signal input from the camera head 5 and outputs the resultant signal to the units configuring the control device 9.

The signal processing unit 92 executes signal processing such as noise reduction processing and A/D conversion processing on the agent observation image information or the subject observation image information input from the camera head 5 via the communication module 91, and outputs the resultant information to the image processing unit 93.

Under the control of the control unit 97, the image processing unit 93 performs various types of image processing on the agent observation image information or the subject observation image information input from the signal processing unit 92 and outputs the resultant information to the display device 7. Here, the predetermined image processing includes various types of known image processing such as interpolation processing, color correction processing, color enhancement processing, and contour enhancement processing. The image processing unit 93 is configured to include a memory and a processor having hardware such as a GPU, an FPGA, or a CPU. In the first embodiment, the image processing unit 93 functions as an image processing device. The image processing unit 93 includes at least a detection unit 931, a clamp processing unit 932, a gain adjustment unit 933, a reduction processing unit 934, a γ correction unit 935, and a superimposition unit 936.

The detection unit 931 detects the brightness of each of the agent observation image information or the subject observation image information input from the signal processing unit 92 and outputs the detection result to the control unit 97. Specifically, the detection unit 931 outputs the brightness of the agent observation image information, based on the pixel values of a plurality of pixels in the agent observation image information, to the control unit 97, and outputs the brightness of the subject observation image information, based on the pixel values of a plurality of pixels in the subject observation image information, to the control unit 97. Specifically, the detection unit 931 outputs, as the brightness of the agent observation image information, the average value of the luminance values of the pixels of the agent observation image information to the control unit 97, and outputs, as the brightness of the subject observation image information, the average value of the luminance values of the pixels of the subject observation image information to the control unit 97.

Under the control of the control unit 97, the clamp processing unit 932 executes clamp processing, for fixing the black level, on the agent observation image information or the subject observation image information input from the signal processing unit 92, and outputs the resultant information to the gain adjustment unit 933.

Under the control of the control unit 97, the gain adjustment unit 933 executes first gain processing, for amplifying the pixel values of a plurality of pixels configuring the agent observation image information, on the agent observation image information, and outputs the resultant information to the reduction processing unit 934. Specifically, under the control of the control unit 97, the gain adjustment unit 933 executes the first gain processing, for amplifying the pixel values of a plurality of pixels configuring the agent observation image information, on the agent observation image information with a larger gain amount set for lower brightness of the agent observation image information detected by the detection unit 931, and outputs the resultant information to the reduction processing unit 934. Furthermore, under the control of the control unit 97, the gain adjustment unit 933 executes second gain processing for amplifying the pixel values of a plurality of pixels configuring the subject observation image information, and outputs the resultant information to the γ correction unit 935. Specifically, under the control of the control unit 97, the gain adjustment unit 933 executes the second gain processing, for amplifying the pixel values of a plurality of pixels configuring the subject observation image information, with a larger gain amount set for lower brightness of the subject observation image information detected by the detection unit 931, and outputs the resultant information to the γ correction unit 935.

Under the control of the control unit 97, the reduction processing unit 934 executes reduction processing, for reducing the pixel values of pixels lower than a predetermined threshold, on the agent observation image information after the first gain processing by the gain adjustment unit 933. Specifically, the reduction processing unit 934 subtracts the predetermined threshold from the pixel value of each pixel in the agent observation image information to reduce the pixel values of pixels lower than the predetermined threshold, with the predetermined threshold set to be higher for a larger gain amount of the first gain processing by the gain adjustment unit 933.

Under the control of the control unit 97, the γ correction unit 935 executes γ correction processing on the agent observation image information after the reduction processing by the reduction processing unit 934, and outputs the resultant information to the display device 7 or the superimposition unit 936. Furthermore, under the control of the control unit 97, the γ correction unit 935 executes γ correction processing on the subject observation image information after the second gain processing by the gain adjustment unit 933, and outputs the resultant information to the display device 7.

Under the control of the control unit 97, the superimposition unit 936 superimposes the agent observation image information on the subject observation image information and outputs the resultant information to the display device 7.

The input unit 94 is configured to include a keyboard, a mouse, a touch panel, and the like. The input unit 94 accepts various types of information input through a user operation.

The memory 95 is configured to include a volatile memory, a nonvolatile memory, a frame memory, and the like. The memory 95 stores various programs executed by the endoscope system 1 and various types of data used during processing. Note that the memory 95 may further include a memory card or the like that is detachably attached to the control device 9.

The output unit 96 is configured to include a speaker, a printer, a display, and the like. The output unit 96 outputs various types of information related to the endoscope system 1.

The control unit 97 performs overall control on the units configuring the endoscope system 1. The control unit 97 is configured to include a memory and hardware such as a CPU.

Processing Executed by Control Device

Figure 3:
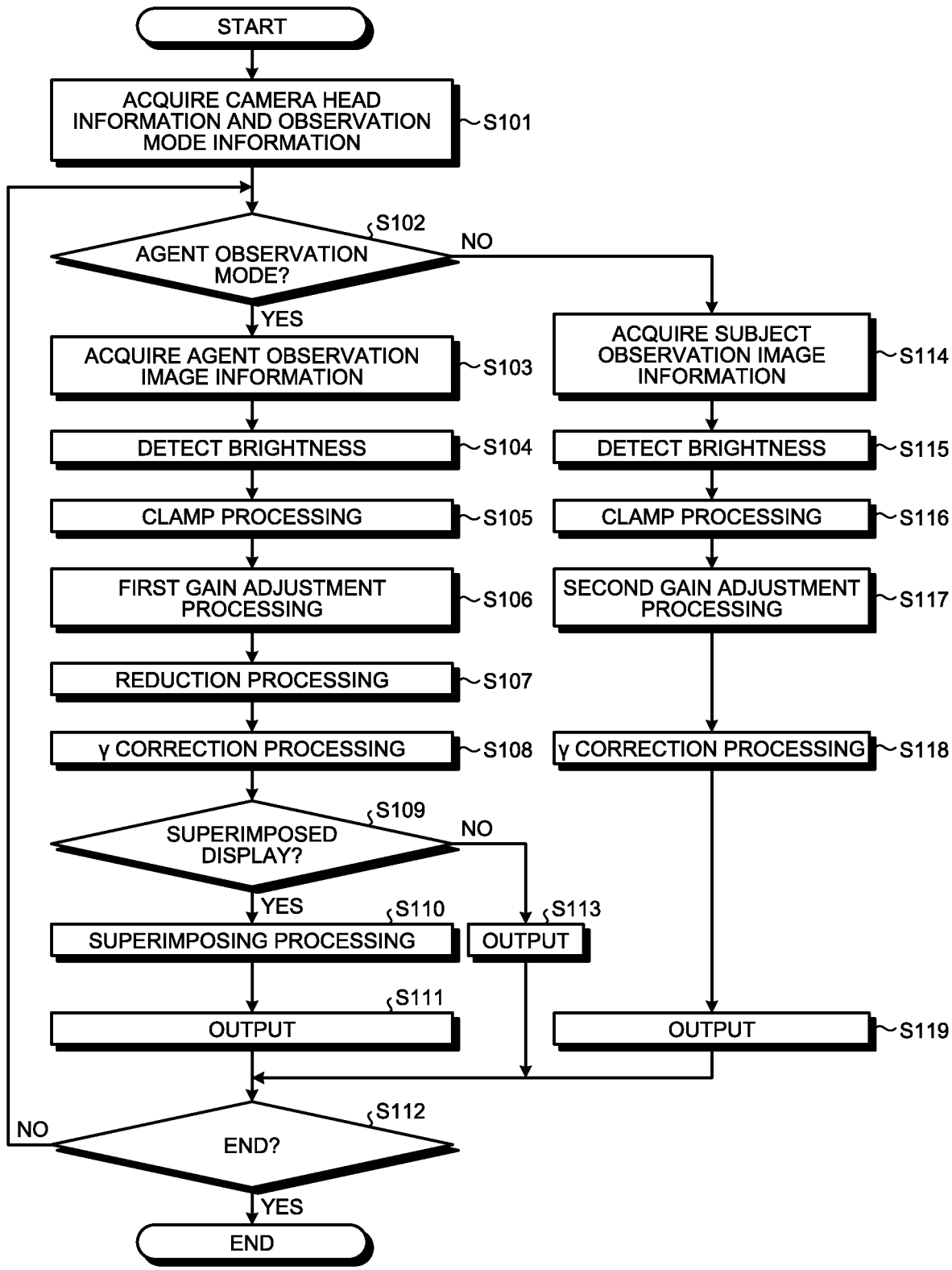
FIG. 3 is a flowchart illustrating an overview of processing executed by the control device according to the first embodiment.

Next, processing executed by the control device 9 will be described. FIG. 3 is a flowchart illustrating an overview of processing executed by the control device 9.

First of all, as illustrated in FIG. 3, the control unit 97 acquires the camera head information from the camera head 5 via the communication module 91 and observation mode information indicating the current observation mode of the endoscope system 1 from the memory 95 (Step S101).

Next, the control unit 97 determines whether the endoscope system 1 is set to be in the agent observation mode (Step S102). When the control unit 97 determines that the endoscope system 1 is set to be in the agent observation mode (Step S102: Yes), the control device 9 proceeds to Step S103 described later. On the other hand, when the control unit 97 determines that the endoscope system 1 is not set to be in the agent observation mode (Step S102: No), the control device 9 proceeds to Step S114 described later. Note that the control unit 97 may determine whether the endoscope system 1 is set to be in the agent observation mode in response to an instruction signal for designating the observation mode input from the input unit 94.

In Step S103, the image processing unit 93 acquires the agent observation image information via the communication module 503, the communication module 91, and the signal processing unit 92, under the control of the control unit 97. The agent observation image information is generated as a result of the imaging unit 502 capturing an image based on light emitted from the agent administered into the subject in response to the infrared light irradiation by the second light source unit 32.

Then, the detection unit 931 detects the brightness of the agent observation image information under the control of the control unit 97 (Step S104). Specifically, the detection unit 931 detects the average value of the pixel values (output values) of the respective pixels in the agent observation image information as the brightness of the agent observation image information, and outputs to the control unit 97, this detection result as information indicating the brightness of the agent observation image information.

Thereafter, under the control of the control unit 97, the clamp processing unit 932 executes the clamp processing, for fixing the black level, on the agent observation image information (Step S105). Specifically, the clamp processing unit 932 adjusts a clamp level, indicating the black level, to a target value based on an output value (pixel value) from an optical black area (a shielded area of the imaging unit 502) included in the agent observation image information. Then, the clamp processing unit 932 outputs the agent observation image information based on the clamp value thus adjusted, to the gain adjustment unit 933.

Referring back to FIG. 3, the description continues for Step S106 and after.

In Step S106, under the control of the control unit 97, the gain adjustment unit 933 executes the first gain processing for amplifying the pixel value (output value) of each pixel in the agent observation image information, based on the information indicating the brightness of the agent observation image information detected by the detection unit 931. Specifically, the gain adjustment unit 933 executes first gain processing for amplifying the pixel value of each pixel of the agent observation image information with the gain amount in the gain processing set to be larger for lower brightness of the agent observation image information.

Then, under the control of the control unit 97, the reduction processing unit 934 executes reduction processing, for reducing the pixel values of pixels lower than a predetermined threshold, on the agent observation image information after the first gain processing by the gain adjustment unit 933 (Step S107).

Figure 4:
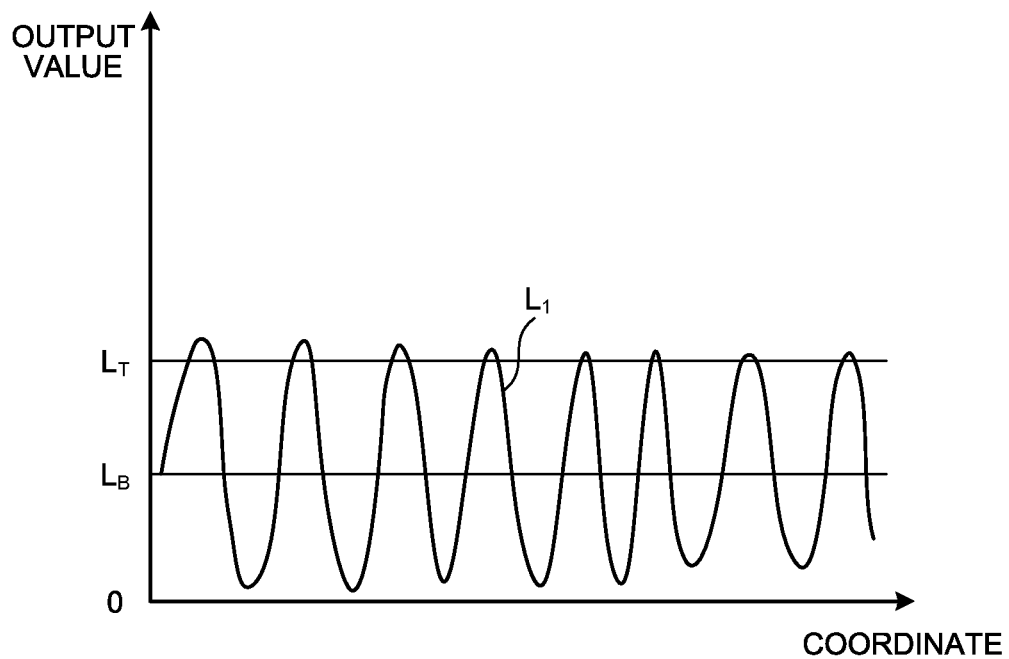
FIG. 4 is a diagram schematically illustrating pixel values of pixels on a predetermined horizontal line in agent observation image information before reduction processing is executed by a reduction processing unit according to the first embodiment.
Figure 5:
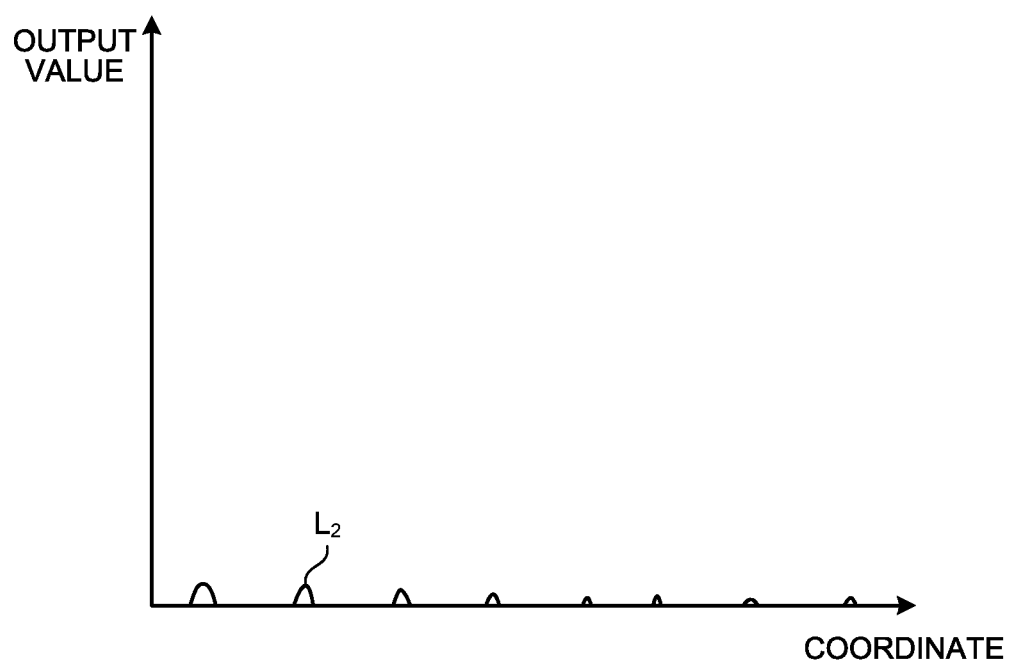
FIG. 5 is a diagram schematically illustrating pixel values of the pixels on the predetermined horizontal line in the agent observation image information after the reduction processing has been executed by the reduction processing unit according to the first embodiment.
Figure 6:
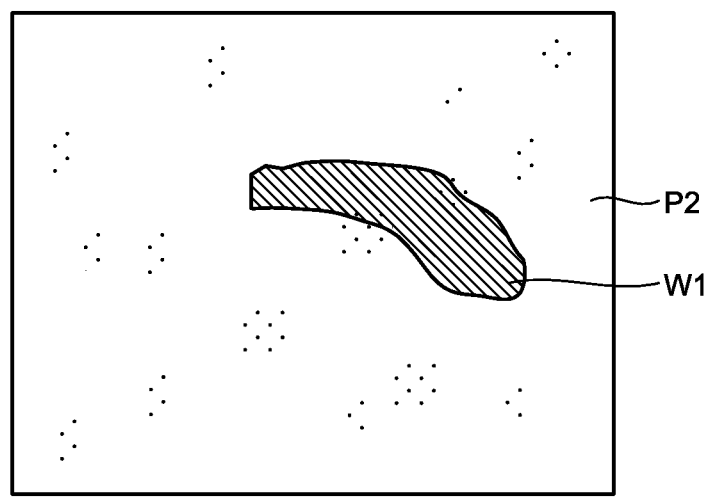
FIG. 6 is a diagram schematically illustrating agent observation image information that has been subjected to the reduction processing by the reduction processing unit according to the first embodiment.
Figure 7:
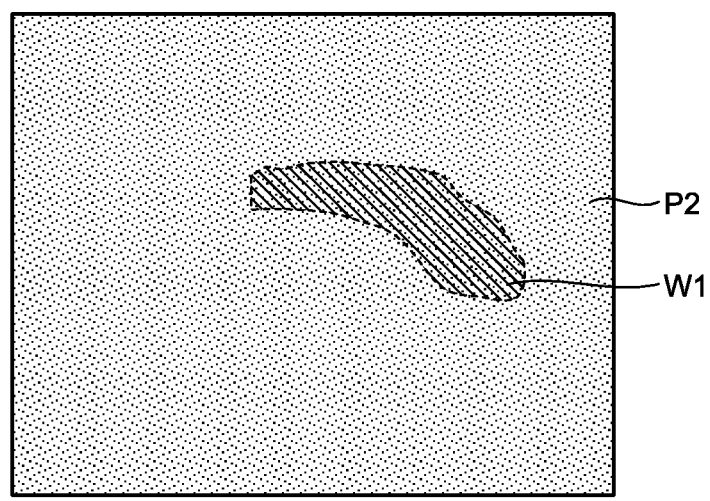
FIG. 7 is a diagram schematically illustrating agent observation image information not subjected to the reduction processing by the reduction processing unit according to the first embodiment.

FIG. 4 is a diagram schematically illustrating pixel values of pixels on a predetermined horizontal line in the agent observation image information before the reduction processing is executed by the reduction processing unit 934. FIG. 5 is a diagram schematically illustrating pixel values of pixels on a predetermined horizontal line in the agent observation image information after the reduction processing is executed by the reduction processing unit 934. FIG. 6 is a diagram schematically illustrating the agent observation image information that has been subjected to the reduction processing by the reduction processing unit 934. FIG. 7 is a diagram schematically illustrating the agent observation image information not subjected to reduction processing by the reduction processing unit 934. In FIGS. 4 and 5, the horizontal axis represents the coordinates of each pixel on a predetermined horizontal line in the agent observation image information, and the vertical axis represents the pixel value (output value) of each pixel in the agent observation image information. In FIG. 4, a curve $L_1$ indicates the pixel value of each pixel on the predetermined horizontal line in the agent observation image information before the reduction processing, and a straight line $L_B$ indicates the clamp value. A straight line $L_T$ indicates a threshold. Furthermore, in FIG. 5, a curve $L_2$ indicates the pixel value of each pixel on the predetermined horizontal line in the agent observation image information after the reduction processing.

As illustrated in FIG. 4, the reduction processing unit 934 reduces the pixel values of the pixels lower than the threshold $L_T$, by performing subtraction of the threshold $L_T$ for each pixel in the agent observation image information (the curve $L_1$ in FIG. 4 to the curve $L_2$ in FIG. 5). In this case, the reduction processing unit 934 changes the threshold $L_T$ based on the gain amount achieved by the gain adjustment unit 933 under the control of the control unit 97. Specifically, under the control of the control unit 97, the reduction processing unit 934 subtracts the threshold $L_T$ from the pixel value of each pixel in the agent observation image information to reduce the pixel values of pixels lower than the threshold $L_T$, with the threshold $L_T$ set to be higher for a larger gain amount achieved by the gain adjustment unit 933. Thus, in agent observation image information P1 illustrated in FIG. 6, a fluorescent region W1 is not buried in noise and thus may be distinguished from the other regions. In contrast, agent observation image information P2 illustrated in FIG. 7 is not subjected to the reduction processing by the reduction processing unit 934, and thus is white as a whole due to noise. Thus, the fluorescent region W1 is buried in noise to be difficult to distinguish from the other regions. As a result, the information is visually recognized that the fluorescence is emitted from the entire region. Note that in FIGS. 6 and 7, noise is schematically is expressed with hatching density.

Referring back to FIG. 3, the description continues for Step S108 and after.

In Step S108, the γ correction unit 935 executes the γ correction processing on the agent observation image information under the control of the control unit 97, and outputs the resultant information (Step S108).

Then, the control unit 97 determines whether a superimposed display mode is set (Step S109). In the superimposed display mode, the endoscope system 1 displays the agent observation image information and the subject observation image information in a superimposed manner. When the control unit 97 determines that the endoscope system 1 is set to be in the superimposed display mode (Step S109: Yes), the control device 9 proceeds to Step S110 described later. On the other hand, when the control unit 97 determines that the endoscope system 1 is not set to be in the superimposed display mode (Step S109: No), the control device 9 proceeds to Step S113 described later.

In Step S110, under the control of the control unit 97, the superimposition unit 936 executes superimposing processing for superimposing the subject observation image information on the agent observation image information.

Figure 8:
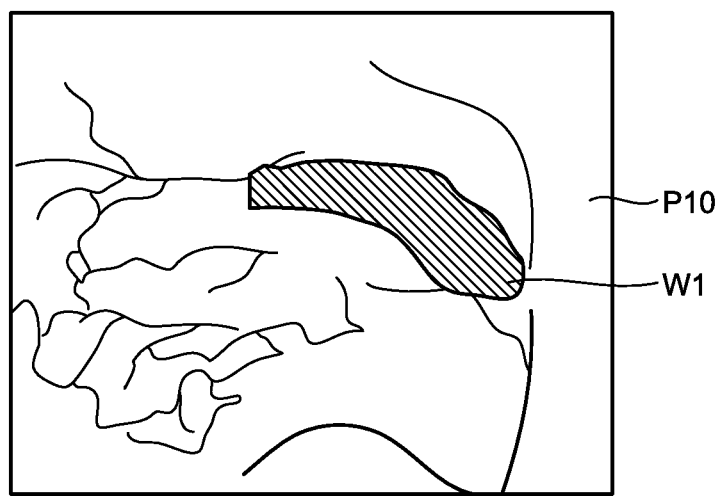
FIG. 8 is a diagram schematically illustrating a superimposed image obtained by superimposing the agent observation image information subjected to the reduction processing by the reduction processing unit on subject observation image information.
Figure 9:
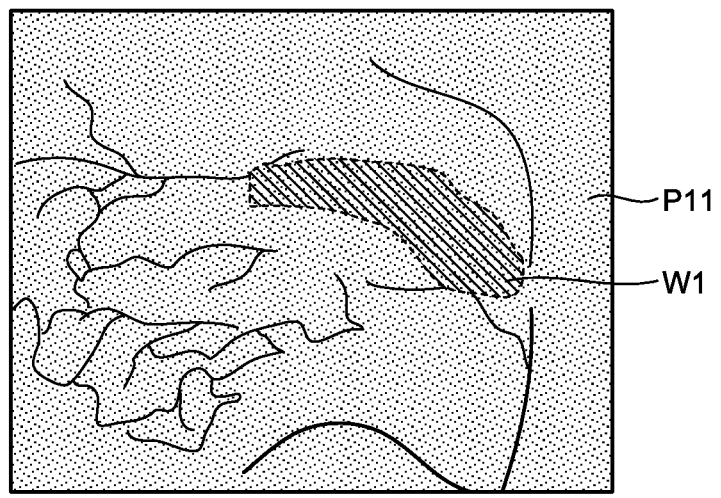
FIG. 9 is a diagram schematically illustrating a superimposed image obtained by superimposing the agent observation image information not subjected to the reduction processing by the reduction processing unit on subject observation image information.

Then, the image processing unit 93 outputs the superimposed image generated by the superimposition unit 936 to the display device 7 under the control of the control unit 97 (Step S111). FIG. 8 is a diagram schematically illustrating a superimposed image obtained by superimposing the agent observation image information subjected to the reduction processing by the reduction processing unit 934 on the subject observation image information. FIG. 9 is a diagram schematically illustrating a superimposed image obtained by superimposing the agent observation image information not subjected to the reduction processing by the reduction processing unit 934 on the subject observation image information. As illustrated in FIG. 8, in a superimposed image P10, the fluorescent region W1 is not buried in noise and thus may be distinguished from the other regions. On the other hand, as illustrated in FIG. 9, a superimposed image P11 is not subjected to the reduction processing by the reduction processing unit 934. Thus, in the image, the fluorescent region W1 is buried in noise and thus is difficult to distinguish from the other regions. Note that in FIG. 9, to express noise, it is schematically is expressed with hatching.

Thereafter, when an instruction signal for ending the observation of the subject is input from the input unit 94 (Step S112: Yes), the control device 9 completes the processing. On the other hand, when the instruction signal for ending the observation of the subject is not input from the input unit 94 (Step S112: No), the control device 9 returns to Step S102 described above.

In Step S113, the image processing unit 93 outputs the agent observation image information subjected to γ correction by the γ correction unit 935 to the display device 7 under the control of the control unit 97. After Step S113, the control device 9 proceeds to Step S112.

In Step S114, the image processing unit 93 acquires the subject observation image information generated by the imaging unit 502 via the communication module 503, the communication module 91, and the signal processing unit 92, under the control of the control unit 97.

Then, the detection unit 931 detects the brightness of the subject observation image information under the control of the control unit 97 (Step S115).

Thereafter, under the control of the control unit 97, the clamp processing unit 932 executes the clamp processing, for fixing the black level, on the subject observation image information (Step S116).

Next, the gain adjustment unit 933 executes the second gain processing for amplifying the pixel value of each pixel in the subject observation image information, under the control of the control unit 97 (Step S117).

Specifically, the gain adjustment unit 933 executes the second gain processing for amplifying the pixel value of each pixel in the subject observation image information with the gain amount in the gain processing set to be larger for lower brightness of the subject observation image information.

Thereafter, the γ correction unit 935 executes the γ correction on the subject observation image information input from the gain adjustment unit 933 (Step S118).

Then, the image processing unit 93 outputs the subject observation image information subjected to the γ correction by the γ correction unit 935 to the display device 7 under the control of the control unit 97 (Step S119). After Step S119, the control device 9 proceeds to Step S112.

According to the first embodiment described above, the image processing unit 93 executes the first gain processing, for amplifying the pixel value, on the agent observation image information generated in the agent observation mode. Then, the reduction processing of reducing the pixel values of pixels lower than the predetermined threshold is executed on the resultant agent observation image information. Thus, the image may be prevented from degrading and noticeable afterimage may be prevented from being produced.

Furthermore, according to the first embodiment, the image processing unit 93 detects the brightness of the agent observation image information. The first gain processing is executed with the gain amount set to be larger for the lower brightness detected. The reduction processing is executed with the predetermined threshold set to be higher for a larger gain amount in the first gain processing. Thus, the pixel value may be reduced with respect to noise enhanced in accordance with the gain, whereby the image quality may be prevented from degrading.

Furthermore, according to the first embodiment, the image processing unit 93 executes the second gain processing on the subject observation image information generated in the subject observation mode, outputs the resultant information to the display device 7 with no reduction processing executed thereon, whereby the image quality may be prevented from degrading in the subject observation mode.

Furthermore, according to the first embodiment, the image processing unit 93 detects the brightness of the subject observation image. The second gain processing is executed with the gain amount set to be larger for the lower brightness of the subject observation image information. Thus, an image with the brightness adjusted may be obtained even when the amount of light reflected from the object is small.

Note that in the first embodiment, the reduction processing unit 934 reduces noise included in the agent observation image information by removing pixel values that are equal to or less than the predetermined threshold in the agent observation image information. Alternatively, for example, the noise included in the agent observation image information may be reduced by multiplying the pixel value that is equal to or less than the predetermined threshold by a predetermined coefficient (0.1 in particular). The predetermined coefficient may be determined by a function or a lookup table using a pixel value as a parameter.

In the first embodiment, the reduction processing unit 934 changes the threshold according to the gain amount in the first gain processing by the gain adjustment unit 933. Alternatively, the threshold may be changed in accordance with the type of the imaging unit 502 in the camera head information or a parameter correlated with the gain amount such as the brightness of the agent observation image information detected by the detection unit 931, the intensity of infrared light and the like supplied by the light source device 3, and a shutter speed of the imaging unit 502.

In the first embodiment, the reduction processing unit 934 reduces the noise included in the agent observation image information by changing the threshold according to the gain amount of the first gain processing by the gain adjustment unit 933. Alternatively, for example, the noise included in the agent observation image information may be reduced by changing the clamp value of the clamp processing unit 932. In this case, the clamp processing unit 932 executes the reduction processing for reducing the noise with the clamp value set to be larger for a larger gain amount in the first gain processing by the gain adjustment unit 933. Thus, the pixel value may be reduced with respect to the noise enhanced in accordance with the gain, whereby the image quality may be prevented from degrading. Furthermore, the clamp processing unit 932 may not only change the clamp value based on the gain amount in the first gain processing by the gain adjustment unit 933 but may also change the clamp value based on the temperature of the imaging unit 502 or the type of the imaging unit 502.

First Modification of First Embodiment

In the first embodiment, the reduction processing unit 934 reduces the noise included in the agent observation image information by changing the threshold according to the gain amount of the first gain processing by the gain adjustment unit 933. Alternatively, for example, the noise included in the agent observation image information may be reduced by changing a tone curve of the γ correction by the γ correction unit 935.

Figure 10:
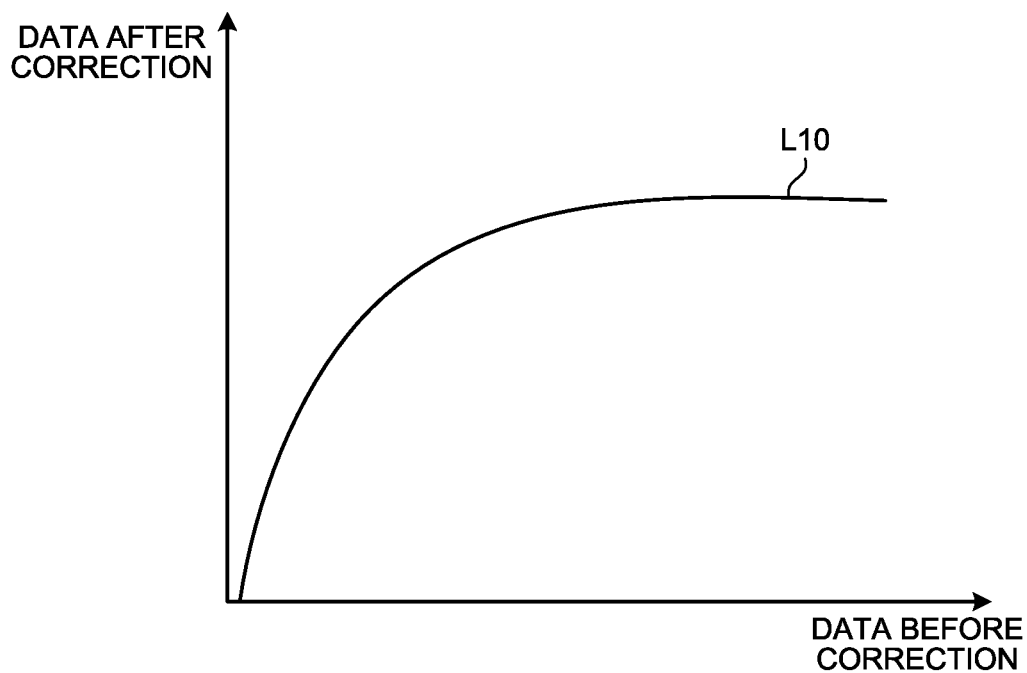
FIG. 10 is a diagram schematically illustrating a tone curve of normal γ correction performed by a γ correction unit according to a modification of the first embodiment.
Figure 11:
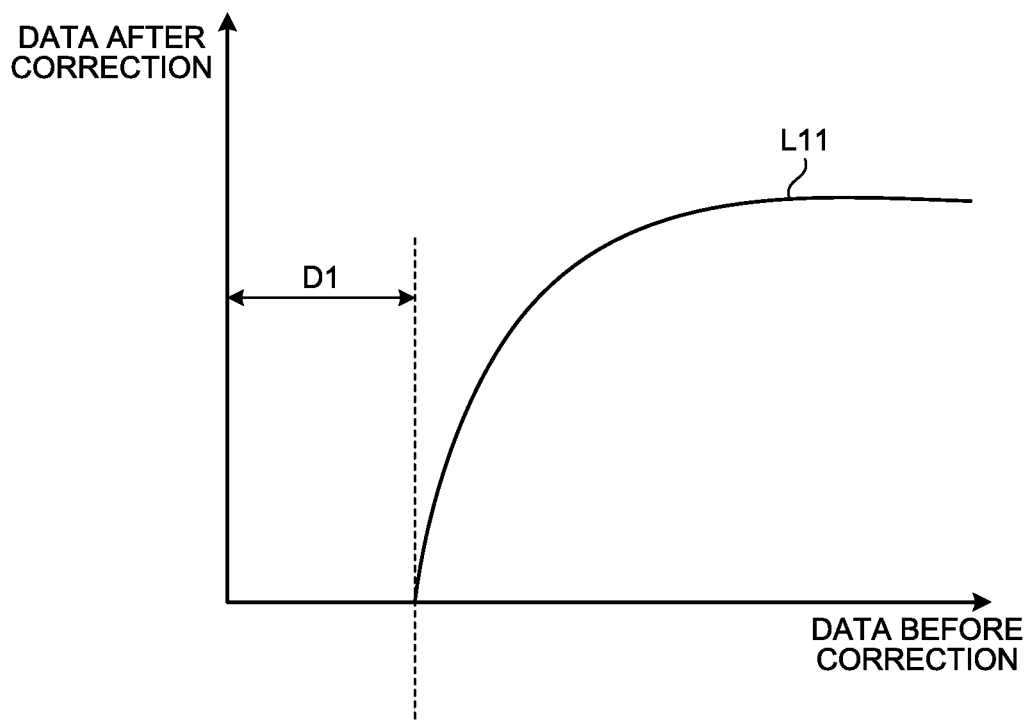
FIG. 11 is a diagram schematically illustrating a tone curve of γ correction performed by the γ correction unit according to the modification of the first embodiment.

FIG. 10 is a diagram schematically illustrating a tone curve of normal γ correction performed by the γ correction unit 935. FIG. 11 is a diagram schematically illustrating a tone curve of γ correction performed by the γ correction unit 935 according to the modification of the first embodiment; In FIGS. 10 and 11, the horizontal axis represents data before correction of the agent observation image information (input data), and the vertical axis represents data after correction of the agent observation image information (output data). In FIG. 10, a curve L10 indicates a normal γ correction tone curve. In FIG. 11, a curve L11 indicates a γ correction tone curve.

As indicated by the curve L10 in FIG. 10, generally, the γ correction unit 935 performs the γ correction on the agent observation image information and outputs the resultant information, under the control of the control unit 97. On the other hand, as illustrated by the curve L11 in FIG. 11, the γ correction unit 935 performs γ correction for removing the pixel values in a range D1 that are expected to be noise from the agent observation image information, and outputs the resultant information, under control of the control unit 97. Note that the γ correction unit 935 changes the range D1 according to the gain amount in the first gain processing by the gain adjustment unit 933 under the control of the control unit 97. Thus, the noise included in the agent observation image information may be reduced.

According to the first modification of the first embodiment described above, the γ correction unit 935 performs the γ correction to remove the pixel values in the range D1 that are expected to be the noise from the agent observation image information, whereby the noise included in the agent observation image information may be reduced.

Figure 12:
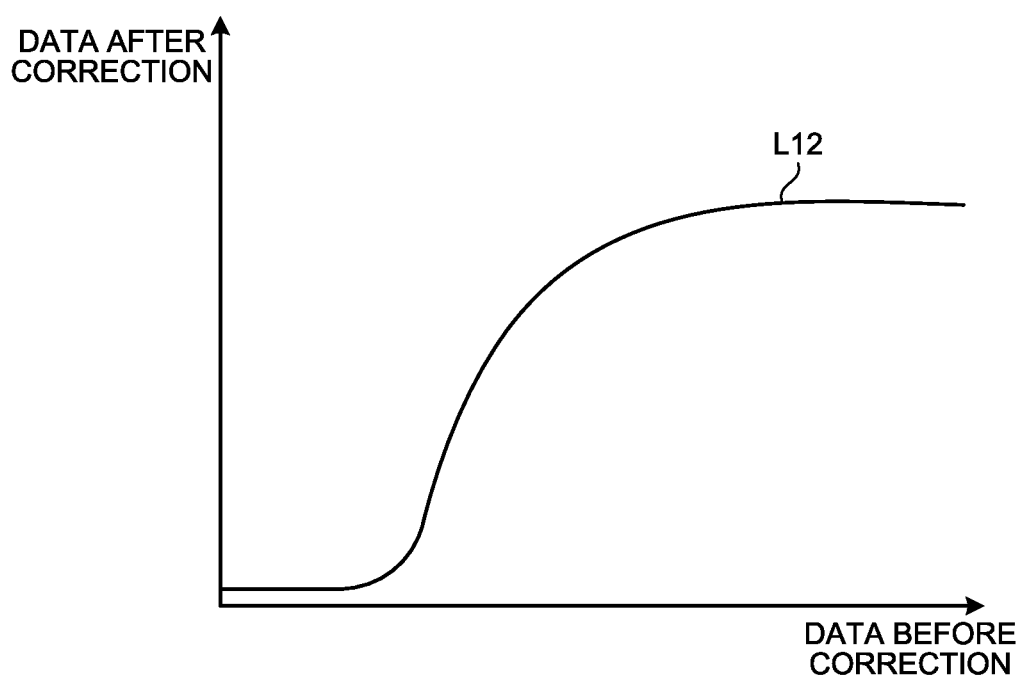
FIG. 12 is a diagram schematically illustrating another tone curve of γ correction performed by the γ correction unit according to the modification of the first embodiment.

In the first modification of the first embodiment, the γ correction unit 935 reduces the noise included in the agent observation image information based on the tone curve for removing the pixel values in the range D1 expected to be noise in the agent observation image information. Alternatively, for example, noise included in the agent observation image information may be reduced based on an S-shaped tone curve such as a curve L12 illustrated in FIG. 12.

In the first modification of the first embodiment, the γ correction unit 935 changes the range D1 of pixel values expected to be noise in accordance with the gain amount in the first gain processing by the gain adjustment unit 933. Alternatively, the range D1 of pixel values expected to be noise may be changed in accordance with the type of the imaging unit 502 included in the camera head information, the brightness of the agent observation image information detected by the detection unit 931, or the intensity of infrared light emitted by the light source device 3. Furthermore, the γ correction unit 935 may not only change the range D1 of pixel values expected to be noise based on the gain amount in the first gain processing by the gain adjustment unit 933, but may also change the range D1 based on the temperature of the imaging unit 502 or the type of the imaging unit 502.

Second Embodiment

Next, a second embodiment will be described. In the first embodiment described above, a case where the present disclosure is applied to a rigid endoscope system using a rigid endoscope is described. In the second embodiment, a case where the present disclosure is applied to a flexible endoscope system using a flexible endoscope is described. Note that the components that are the same as those in the endoscope system 1 according to the first embodiment described above are denoted by the same reference numerals, and detailed description thereof is omitted.

Schematic Configuration of Endoscope System

Figure 13:
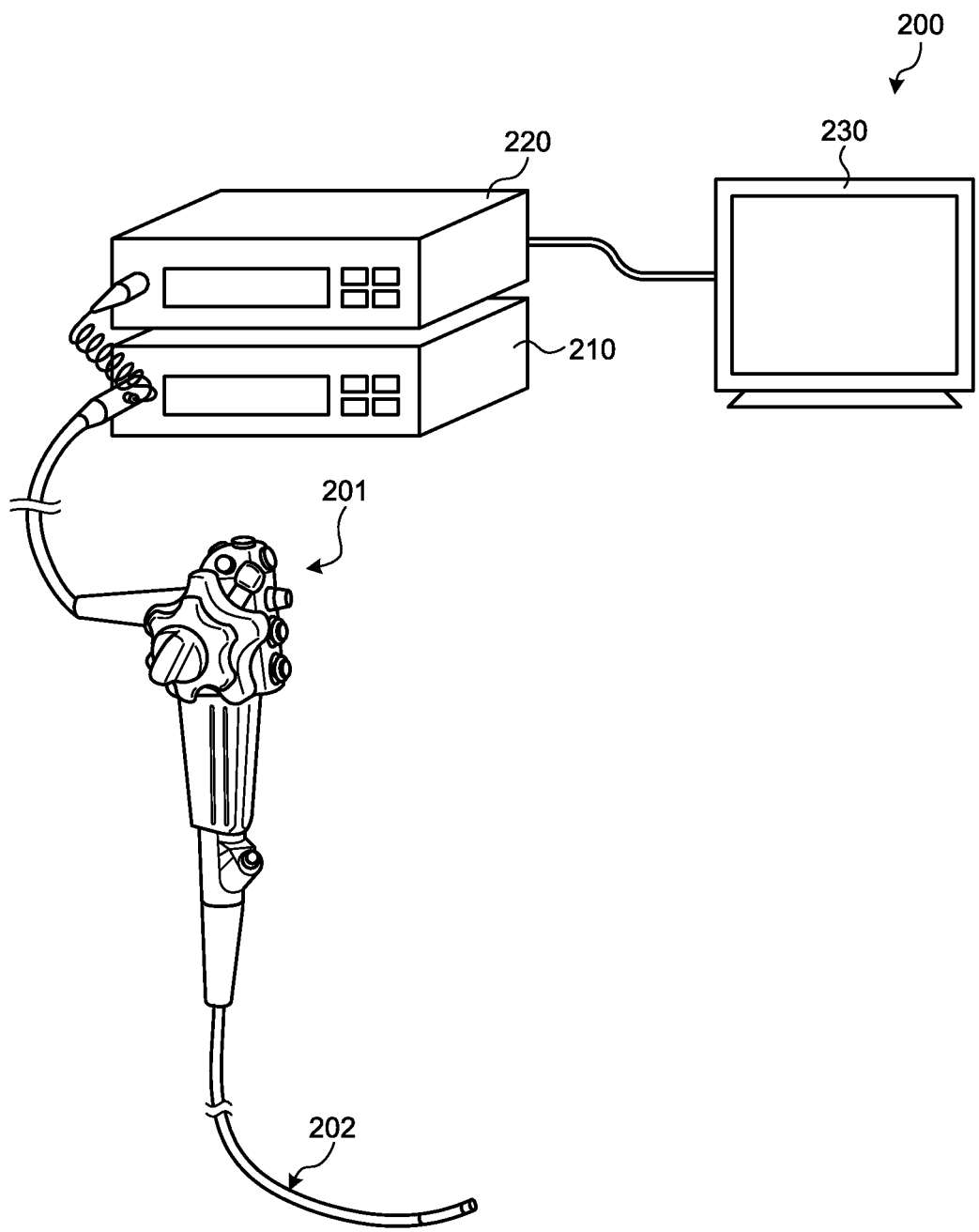
FIG. 13 is a diagram illustrating a schematic configuration of an endoscope system according to a second embodiment.
Figure 14:
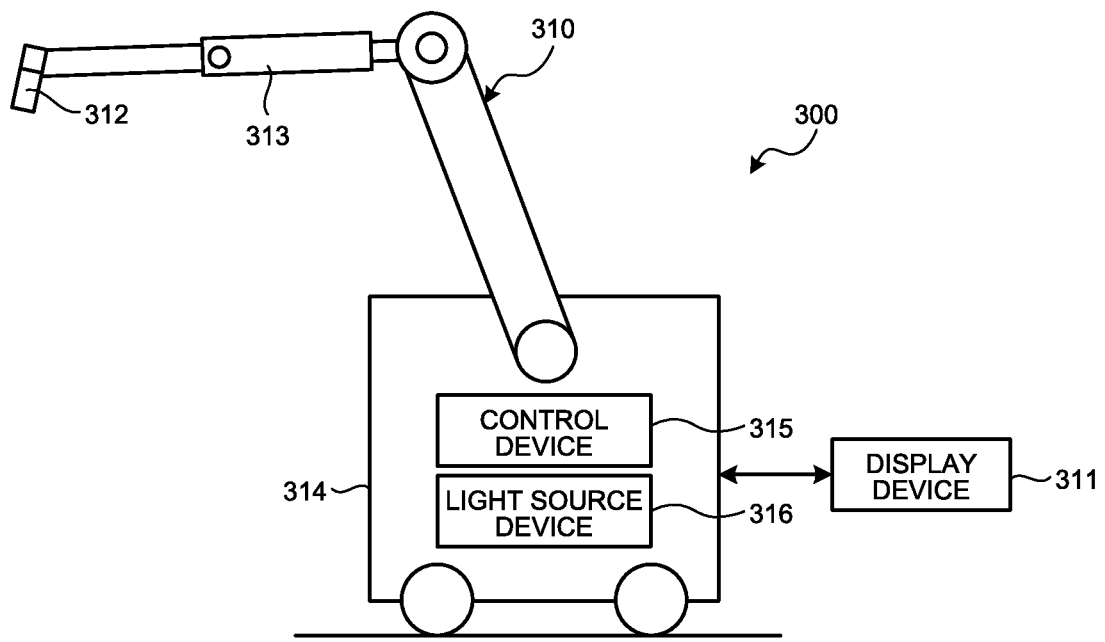
FIG. 14 is a diagram illustrating a schematic configuration of a surgical microscope system according to a third embodiment.

FIG. 13 is a diagram illustrating a schematic configuration of an endoscope system according to the second embodiment. An endoscope system 200 illustrated in FIG. 13 includes an endoscope 201 that captures an in-vivo image of an observation region with an insertion portion 202 inserted into a subject and generates a captured image signal, a light source device 210 that supplies white light or infrared light to the endoscope 201, a control device 220 that executes predetermined image processing on the captured image signal acquired by the endoscope 201 and performs overall control on the operation of the endoscope system 200 as a whole, and a display device 230 that displays the in-vivo image that has been subjected to the image processing by the control device 220.

The endoscope 201 includes at least the lens unit 501 and the imaging unit 502 described above.

The light source device 210 includes at least the first light source unit 31, the second light source unit 32, and the light source control unit 33 described above.

The control device 220 includes at least the communication module 91, the signal processing unit 92, the image processing unit 93, the input unit 94, the memory 95, the output unit 96, and the control unit 97 described above.

According to the second embodiment described above, the effects that are the same as those obtained by the first embodiment described above may be obtained with the flexible endoscope system 200.

Third Embodiment

Next, a third embodiment will be described. In the first and the second embodiments described above, the present disclosure is applied to the endoscope system. In the third embodiment, a case where the present disclosure is applied to a surgical microscope system is described. Note that the components that are the same as those in the endoscope system 1 according to the first embodiment described above are denoted by the same reference numerals, and detailed description thereof is omitted.

Configuration of Surgical Microscope System

FIG. 15 is a diagram illustrating a schematic configuration of a surgical microscope system according to the third embodiment. A surgical microscope system 300 illustrated in FIG. 15 includes a microscope device 310 that is a medical imaging device that captures and acquires an image for monitoring an object, and a display device 311 that displays the image captured by the microscope device 310. Note that the display device 311 and the microscope device 310 may be integrally formed.

The microscope device 310 includes a microscope unit 312 that captures an enlarged image of a minute part of an object, a support unit 313 that includes an arm connected to a proximal end portion of the microscope unit 312 and rotatably supports the microscope unit 312, and a base unit 314 that rotatably holds a proximal end portion of the support unit 313 and is movable on the floor surface. The base unit 314 includes a control device 315 that controls the operation of the surgical microscope system 300, and a light source device 316 that generates white light, infrared light, or the like to be emitted onto an object from the microscope device 310. Note that the control device 315 includes at least the communication module 91, the signal processing unit 92, the image processing unit 93, the input unit 94, the memory 95, the output unit 96, and the control unit 97 described above. In addition, the light source device 316 includes at least the first light source unit 31, the second light source unit 32, and the light source control unit 33 described above. In addition, the base unit 314 may be configured to support the support unit 313 by being fixed to a ceiling, a wall surface, or the like, instead of being movably installed on the floor surface.

The microscope unit 312 has a cylindrical shape, for example, and includes the lens unit 501 and the imaging unit 502 described above. The microscope unit 312 has a side surface provided with a switch that receives an input of an operation instruction for the microscope device 310. A cover glass member for protecting the inside is provided on an opening surface at the lower end of the microscope unit 312 (not illustrated).

With the surgical microscope system 300 configured as described above, a user such as a practitioner holding the microscope unit 312 moves the microscope unit 312, performs a zooming operation, and switches illumination light, while operating various switches. Note that the microscope unit 312 preferably has a shape elongated in the observation direction so that the user may easily hold the microscope unit 312 and change the viewing direction. Thus, the shape of the microscope unit 312 may be a shape other than a cylindrical shape, and may be, for example, a polygonal column shape.

With the third embodiment described above, the effects that are the same as those obtained by the first embodiment described above may be obtained with the surgical microscope system 300.

Other Embodiments

Variations may be formed by appropriately combining a plurality of components disclosed as the medical observation systems according to the first to third embodiments of the present disclosure described above. For example, some components may be deleted from all the components described in the medical observation system according to the first to third embodiments of the present disclosure described above. Furthermore, the components described in the medical observation system according to the first to third embodiments of the present disclosure described above may be appropriately combined.

In the medical observation system according to the first to third embodiments of the present disclosure, a "unit" described above may be read as "means", "circuit", and the like. For example, the control unit may be read as control means or a control circuit.

A program to be executed by the medical observation system according to the first to third embodiments of the present disclosure is file data in an installable format or an executable format, and is provided by being recorded on a computer-readable recording medium such as a CD-ROM, a flexible disk (FD), a CD-R, a digital versatile disk (DVD), a USB medium, or a flash memory.

Furthermore, the program to be executed by the medical observation system according to the first to third embodiments of the present disclosure may be configured to be provided by being stored on a computer connected to a network such as the Internet and downloaded via the network.

In the description of the timing charts in the present specification, the context of processes between timings is clearly indicated using expressions such as "first", "then", "next", etc. However, the order of the processes for implementing the present disclosure is not uniquely determined by their expressions. That is, the order of processes in the timing charts described in this specification may be changed within a consistent range. As described above, some of the embodiments of the present application have been described in detail with reference to the drawings. However, these are merely examples, and the present disclosure may be carried out, including the aspects described in the disclosure section of the present disclosure and other aspects with various modifications and improvements, based on the knowledge of those skilled in the art.

According to the present disclosure, it is possible to suppress the resolution degradation and to prevent notable afterimage from being produced efficiently.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An image processor comprising:
   circuitry configured to:
   receive agent observation image information including information of a plurality of pixels obtained by capturing an image based on fluorescence from a subject administered with an agent that emits fluorescence upon being irradiated with excitation light in a predetermined wavelength band;
   amplify pixel values of the plurality of pixels by executing first gain processing on the agent observation image information; and
   after first gain processing, further reduce pixel values of each of the plurality of pixels by subtracting a predetermined threshold for each of the plurality of pixels in the agent observation image information.

2. The image processor according to claim 1, wherein the circuitry is configured to:
   detect brightness of the agent observation image information from the pixel values of the plurality of pixels in the agent observation image information; and
   set a larger gain amount in the first gain processing for lower brightness, wherein
   the predetermined threshold set to be higher for larger gain amount.

3. The image processor according to claim 1, wherein the circuitry is configured to use a function or a lookup table with the pixel values serving as parameters to determine the predetermined threshold.

4. The image processor according to claim 1, wherein the circuitry is configured to:
   amplify pixel values of a plurality of pixels in subject observation image information including information of the plurality of pixels obtained by capturing an image based on light reflected from the subject by executing second gain processing; and
   output the subject observation image information after the second gain processing to outside, without executing the subtracting.

5. The image processor according to claim 4, wherein
   brightness of the subject observation image information is detected based on the pixel values of the plurality of pixels in the subject observation image information, and
   a larger gain amount in the second gain processing is for the lower brightness of the subject observation image information.

6. An image processing method comprising:
   receiving agent observation image information including information of a plurality of pixels obtained by capturing an image based on fluorescence from a subject administered with an agent that emits fluorescence upon being irradiated with excitation light in a predetermined wavelength band;
   amplifying pixel values of the plurality of pixels by executing first gain processing on the agent observation image information; and after first gain processing, further reducing pixel values of each of the plurality of pixels subtracting a predetermined threshold for each of the plurality of pixels in the agent observation image information.

7. A non-transitory computer readable recording medium on which an executable program for processing an image, the program instructing a processor to execute:
receiving agent observation image information including information of a plurality of pixels obtained by capturing an image based on fluorescence from a subject administered with an agent that emits fluorescence upon being irradiated with excitation light in a predetermined wavelength band;
amplifying pixel values of the plurality of pixels by executing first gain processing on the agent observation image information; and
after first gain processing, further reducing pixel values of each of the plurality of pixels by subtracting a predetermined threshold for each of the plurality of pixels in the agent observation image information.

8. The non-transitory computer readable recording medium according to claim 7, the program instructing the processor to execute:
amplifying pixel values of a plurality of pixels in subject observation image information including information of the plurality of pixels obtained by capturing an image based on light reflected from the subject by executing second gain processing; and
outputting the subject observation image information after the second gain processing to outside, without executing the subtracting.

9. The non-transitory computer readable recording medium according to claim 8, the program instructing the processor to execute:
brightness of the subject observation image information is detected based on the pixel values of the plurality of pixels in the subject observation image information, and
a larger gain amount in the second gain processing is for the lower brightness of the subject observation image information.

10. The image processing method according to claim 6, further comprising:
amplifying pixel values of a plurality of pixels in subject observation image information including information of the plurality of pixels obtained by capturing an image based on light reflected from the subject by executing second gain processing; and
outputting the subject observation image information after the second gain processing to outside, without executing the subtracting.

11. The image processing method according to claim 10, further comprising:
brightness of the subject observation image information is detected based on the pixel values of the plurality of pixels in the subject observation image information, and
a larger gain amount in the second gain processing is for the lower brightness of the subject observation image information.

* * * * *